United States Patent
Kennedy et al.

(10) Patent No.: US 9,070,357 B1
(45) Date of Patent: Jun. 30, 2015

(54) USING SPEECH ANALYSIS TO ASSESS A SPEAKER'S PHYSIOLOGICAL HEALTH

(75) Inventors: Peter Kennedy, Weston, FL (US); Brian K. Buchheit, Davie, FL (US)

(73) Assignee: Brian K. Buchheit, Davie, FL (US)

( * ) Notice: Subject to any disclaimer, the term of this patent is extended or adjusted under 35 U.S.C. 154(b) by 378 days.

(21) Appl. No.: 13/469,616

(22) Filed: May 11, 2012

Related U.S. Application Data

(60) Provisional application No. 61/485,102, filed on May 11, 2011.

(51) Int. Cl.
    *G10L 21/00*     (2013.01)
    *G10L 15/00*     (2013.01)

(52) U.S. Cl.
    CPC ..................... *G10L 15/00* (2013.01)

(58) Field of Classification Search
    CPC ........ G10L 15/00; G10L 15/01; G10L 15/02; G10L 15/04; G10L 15/06; G10L 17/00; G10L 17/06; G10L 17/26
    USPC ............. 704/270, 246, 250, 251, 255, 270.1, 704/274
    See application file for complete search history.

(56) References Cited

U.S. PATENT DOCUMENTS

| | | | | |
|---|---|---|---|---|
| 6,006,188 A | * | 12/1999 | Bogdashevsky et al. | ...... 704/270 |
| 6,055,501 A | * | 4/2000 | MacCaughelty | ............. 704/272 |
| 2006/0036440 A1 | * | 2/2006 | Kunkel | ......................... 704/270 |

\* cited by examiner

*Primary Examiner* — Qi Han
(74) *Attorney, Agent, or Firm* — Patents on Demand, P.A.; Brian K. Buchheit; Scott M. Garrett

(57) ABSTRACT

A method for using speech analysis to detect speech pathologies can begin with registration of a patient with a speech-based health monitor. A speech segment baseline representing an initial state of the patient's speech system can be established for the patient. When prompted, the patient can submit a speech segment representing a current state of the patient's speech system to the speech-based health monitor. The speech-based health monitor can analyze the submitted speech segment using the established speech segment baseline and/or a speech segment history that comprises speech segments previously submitted by the patient. Based upon said analysis, satisfaction of a health alert definition can be determined. A health alert definition can define an action performed by the speech-based health monitor when its associated triggering conditions are satisfied. The action associated with the at least one satisfied health alert definition can then be executed.

20 Claims, 6 Drawing Sheets

100

USING SPEECH ANALYSIS TO ASSESS A SPEAKER'S PHYSIOLOGICAL HEALTH

BACKGROUND

The present invention relates to the field of speech analysis.

A patient's clinical outcome is usually better the earlier a healthcare professional is able to detect and diagnosis their pathology. Health screenings for skin cancer are easily administered and are sometimes sponsored by community groups, often without charge to the patient. In contrast, pulmonary diagnostic tests are generally difficult to administer and require a high degree of cooperation from patients.

Pulmonary baseline screenings are used in some industrial settings where a worker might inadvertently be exposed to toxic or caustic chemicals that may cause pulmonary damage. Taking a baseline on the first day of employment and then again after an incident occurs may aid a physician in determining if the worker has sustained any respiratory damage. If there are changes from the baseline, the physician may order a complete diagnostic battery of tests in order to assess the extent of the injury.

Present technology requires the conscious cooperation of the patient in order to create a useful baseline measurement. A trained medical professional normally administers the baseline pulmonary screening, which can be a costly endeavor. This cost and level of commit before a screening is conducted may function as an entry barrier to having any screening done.

DETAILED DESCRIPTION

Figure 1:
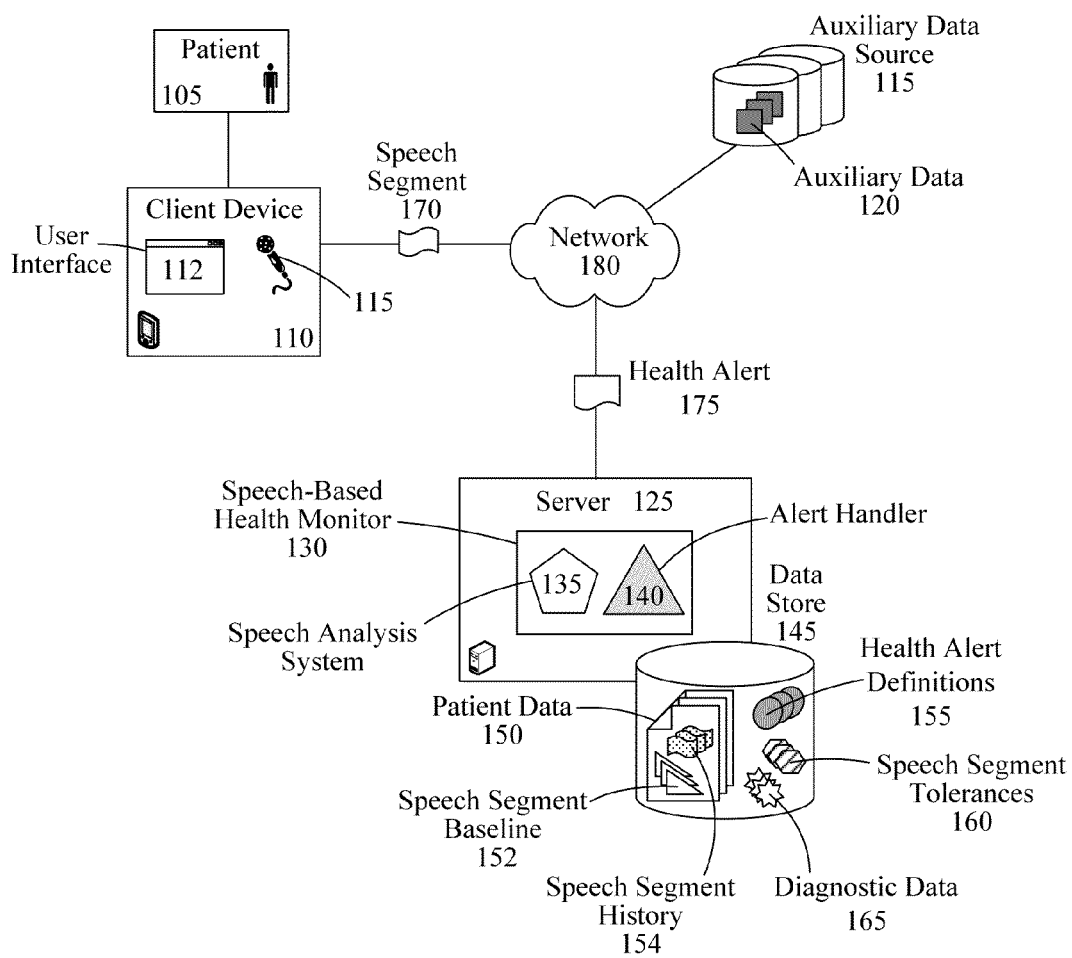
FIG. 1 is a schematic diagram illustrating a system that utilizes speech analysis to assess a speaker's health in accordance with embodiments of the inventive arrangements disclosed herein.

Embodiments of the present invention discloses a solution for using speech analysis to detect pathologies of a speaker. That is, speech of a speaker can be analyzed to assess a speaker's physiological heath. Embodiments of the invention are advantageous as they are passive (non-intrusive to the human body), they can be performed quickly with minimal cost, and they can situationally be performed without requiring specialized medical equipment. In one embodiment, the speech analysis can be performed as a pre-screening step, which if there is a significant likelihood (from the speech-based analysis) of a pathology, more comprehensive (and expensive) tests can be merited. The speech analysis for pathologies does not have significant costs and inconveniences, which sometimes inhibit early detection of pathologies using conventional techniques.

In contemplated embodiments, a speaker may not even be aware that the speech analysis for possible pathologies is occurring. For example, a health care insurer can automatically perform speech analysis of an existing or potential client to determine risks involved in insuring such a person. Medical facilities can perform the speech analysis as part of a patient intake, which provides a physician with results of the analysis to more accurately and cost effectively assess a patient's health. Situations are contemplated, where some prescriptions for medications can be conducted using virtual doctors or by online consolations with physicians. In such situations, speech analysis results for specific pathologies can be a prerequisite to being able to receive some prescriptions without an in-person medical consultation. Additionally, it is contemplated that the speech analysis results can be part of a suite or set of automated assessment measures performed during a health assessment, such as by a kiosk that helps assess a user's health. In other contemplated embodiments, speech received via a computing device can be analyzed for direct marketing purposes. For example, if a speaker's analysis results indicate a high likelihood that the speaker has a cold, tailored advertisements for cold remedies can be presented to the user.

In one embodiment, a patient-centric approach can be embodied by a speech-based health monitor. The speech-based health monitor can establish a speech segment baseline representing the initial state of the patient's speech system. Over time, the patient can submit speech segments representing the current state of the patient's speech system to the speech-based health monitor. The speech-based health monitor can analyze the submitted speech segments to identify changes in the patient's speech characteristics. The degree of these changes can be evaluated using a set of health alert definitions that define actions to take when the degree of a change is outside a predefined speech segment tolerance. The speech-based health monitor can generate and send a health alert to the patient and/or a healthcare professional to expedite handling of a change in the patient's speech that can indicate the onset of a speech pathology.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1 is a schematic diagram illustrating a system 100 that utilizes speech analysis to assess a health of a speaker in accordance with embodiments of the invention. For example, respiratory/laryngeal changes can be analyzed and compared against an expected baseline, where comparison results indicate a statistical likelihood of any of a set of pathological conditions. In system 100, the patient 105 can submit a speech segment 170 from a client device 110 using a user interface 112 for a speech-based health monitor 130 and a microphone 115. The patient 105 may or may not be aware that the microphone is recording the speaker's voice. Further, the microphone 115 and speech segment 170 may be captured as part of an unrelated (to pathologies of a patient 105) function. For example, the patient 105 can be participating in a real-time voice communication (e.g., a phone call) using device 110, where the health assessment is performed in a routine and transparent manner.

The client device 110 can represent a variety of computing devices capable of supporting operation of the user interface 112 and communicating with software application 135 over the network 180. The client device 110 can be configured with a microphone 115, either internally integrated or externally connected, for capturing audio data like speech segment 170.

Examples of the client device 110 can include, but are not limited to, a desktop computer, a laptop computer, a tablet computing device, a smart phone, a computer kiosk, a portable gaming device, a portable multi-media electronic device, and the like.

The user interface 112 can be a graphical interaction mechanism that allows the patient 105 to perform operations and/or interact with the speech-based health monitor 130. For example, the user interface 112 can guide the patient 105 through the process of creating and submitting a speech segment 170 as well as present a variety of information from the speech-based health monitor 130 to the patient 105. For example, the health assessment based on speech can be implemented using a user selected (and installed) application running on device 110.

In another example, the user interface 112 can be one that only provides a visual notification to a patient 105 is a health risk is determined. For example, a "pop-up" notification can be presented to the patient 105 that indicates that the patient 105 has a significant likelihood of having a pathology and that further screening is recommended. In another example, the user interface 112 can present advertisements targeting a pathology or health condition that a patient 105 may have. For instance, if a patient's 105 speech indicates that there is a high likelihood that the patient is in a latter trimester of being pregnant (i.e., the unborn's position impacts a mother's respiration and speech), then baby-specific advertising can be presented within user interface 112. In still another embodiment, a different device (than the one that captured speech and that is used by the patient 105) can be provided a notification of a possible health concern. Caretakers of patient 105, physician's or nurses charged with health care of the patient 105, guardians of patient 105 (for those patient's not of an age of maturity or who are otherwise incompetent/incapacitated), insurers' of patient 105 (which may encourage the patient 105 to be screened for a health condition reducing overall costs through early detection), and the like can be given health-based results in various contemplated embodiments of the invention (which is explicitly not limited to only notifying the patient 105). In situations where privacy concerns exist, redacting of patient identity and/or other confidential elements of the health care assessment from entities lacking a need to know can occur.

As used herein, a speech segment 170 can represent a discrete portion of audio data. The contents of the speech segment 170 can be spoken by the patient 105 and captured by the microphone 115 of the client device 110. Depending upon the specific implementation of the present invention, the speech segment 170 can represent a predetermined phrase or set of sounds spoken by the patient 105. In one embodiment, the health assessment can occur without determining words or content spoken during a conversation. Further, as mentioned, the speech segment 170 can be intentionally manipulated to obscure linguistic meaning being conveyed. Thus, a privacy of the conversation from which the speech segment 170 is acquired can be preserved in embodiments where this is beneficial. For example, the speech segment 170 assessed for health reasons can include a series of discontinuous speech elements. That is, the ordering of spoken output can be intentionally randomized or sampled so as to make the underlying conversation undeterminable. Nonetheless, the speech segment can be analyzed for health-related purposes. Similarly, samples of speech maintained in a data store 145 for a patient's 105 baseline can be intentionally manipulated to ensure spoken words/phrases by the patient are not maintained, thereby providing assurances that linguistically conveyed meanings from conversations in which the speech segment 170 was generated remain private—yet health analysis significant information from spoken communications can be maintained.

The speech-based health monitor 130 can be a software application operating upon a networked server 125 configured to utilize the speech segments 170 to detect changes in various aspects (e.g., rate of speech, diction, inflection, etc.) of the patient's 105 speech over time, which can be an early indication of a pathological condition or disease involving the patient's 105 respiratory system and/or physiology. Since early detection greatly improves a patient's 105 overall survivability, this embodiment of the present invention can be considered a life-saving, non-invasive diagnostic tool.

The speech-based health monitor 130 can include a speech analysis system 135, alert handler 140, and data store 145 containing patient data 150, health alert definitions 155, speech segment tolerances 160, and diagnostic data 165. The speech analysis system 135 can be a component of the speech-based health monitor 130 that processes and/or analyzes speech segments 170 received from the patient 105. Examples of functionality that can be provided by the speech analysis system 135 can include, but are not limited to, cropping a speech segment 170 to contain only the words, phrase, or sounds being studied, filtering background noise, normalizing or amplifying the speech segment 170 (for consistent sampling), speech recognition, and the like.

Once a speech segment 170 is processed by the speech analysis system 135, the speech segment 170 can be stored in the patient data 150 corresponding to submitting patient 105. Patient data 150 can be a collection of various patient-specific data items used by the speech-based health monitor 130. As shown in system 100, the patient data 150 can contain one or more speech segment baselines 152 and a speech segment history 154. The patient data 150 can also be used to store other, general and/or health information (not shown) about the patient 105 like notification preferences and allergies.

A speech segment baseline 152 can represent an initial or standard speech segment 170 used as a basis of comparison for subsequently submitted speech segments 170 to identify changes. A patient 105 can have multiple speech segment baselines 152; each speech segment baseline 152 can represent a different phrase or set of sounds that highlights physiological usage differences of the patient's 105 speech-generating anatomy.

For example, a speech segment baseline 152 can be created that contains words that exemplify the three sounds that require additional resonance in the nasal cavities: the /m/, /n/, and /ŋ/. The word "mining" can be one such word that contains these sounds. The production of any one of these three sounds can require the velopharyngeal port to remain open or unobstructed by the velum (soft palette). In essence, the speech segment baseline 152 can represent the patient's 105 current physiological ability for closing/opening the velopharyngeal port to make these sounds. Therefore, deviations from this specific speech segment baseline 152 can indicate a weakening in the levator palatine, the primary muscle for moving the velum, or the presence of a body like mucus or a tumor that is compromising normal functionality.

The speech segment history 154 can be a collection of the speech segments 170 submitted by a patient 105. Cataloging and/or storage of the speech segments 170 within the speech segment history 154 can be implemented in variety of ways, depending upon the specific design of the speech-based health monitor 130. The speech segment history 154 can be useful to determine speech-related changes for a specific person (e.g., patient 105) over a time period. Thus, the analysis of the speech segment 170 for health assessment can be personalized in one embodiment. In one embodiment, samples from different patients 105 can be taken and assessed. These different people may share a specific health condition, which is known. Commonalities among this set of people can be used to determine new markets for that specific condition. Thus, the speech segment history 154 can be used as a repository to identify new physiological conditions over time. Further, feedback loops and learning algorithms can be employed to leverage known information and speech segment histories 154 to continuously improve speech-based health/pathology analysis breadth and accuracy.

The analysis of a speech segment 170 to a speech segment baseline 152 or the speech segment history 154 can utilize speech segment tolerances 160 and diagnostic data 165. The speech segment tolerances 160 can represent an amount that a parameter of a newly-received speech segment 170 is allowed to deviate from its corresponding value expressed in the speech segment baseline 152 without being considered as indicating a potential respiratory/laryngeal problem.

For example, a speech segment tolerance 160 of "−2 Hz" can be defined for the frequency or pitch of a speech segment 170 to express that a decrease in the frequency of a speech segment 170 from its speech segment baseline 152 of up to 2 Hz is an acceptable condition; decreases greater than 2 Hz can signify a detrimental change in physiology and require further evaluation by a healthcare professional.

The speech segment tolerances 160 can be used in the health alert definitions 155 to define conditions under which a health alert 175 is issued and other actions initiated by the speech-based health monitor 130 on behalf of the patient 105. Evaluation of the health alert definitions 155 and subsequent issuance of the health alert 175 can be performed by the alert handler 140 component of the speech-based health monitor 130. A health alert 175 can be an electronic message sent over the network 180 to the patient 105 or another entity (not shown), such as a doctor or emergency medical technicians (EMTs).

For example, a health alert definition 155 can indicate that a health alert 175 requesting the patient 105 to resubmit the speech segment 170 when analysis of the speech segment 170 indicates that three or more characteristics are outside of their defined speech segment tolerances 160. When the alert handler 140 evaluates the conditions of this health alert definition 155 to be true, the alert handler 140 can then generate and send the appropriate health alert 175 to the patient 105.

The significance of changes in a speech segment 170 can be defined in the diagnostic data 165. Essentially, the diagnostic data 165 can ascribe different combinations of changes within a speech segment 170 to possible problems being experienced by the patient 105. The diagnostic data 165 can be predefined in conjunction with a qualified healthcare professional.

For example, analysis of a speech segment 170 can indicate that the patient's 105 rate of speech is outside of its speech segment tolerance 160. A health alert definition 155 can specify that handling of this occurrence requires a health alert 175 expressing the change and a list of possible pathological causes, which the speech-based health monitor 130 would generate using the diagnostic data 165.

The results of querying the diagnostic data 165 can be filtered based upon patient data 150 and/or auxiliary data 120 obtained from one or more auxiliary data sources 115. An auxiliary data source 115 can represent a data system that is external to, but accessible by the speech-based health monitor 130 over the network 180.

For example, a database 115 of medical records 120 maintained by the patient's 105 doctor can be used to remove improbable causes or to prioritize the possible causes of the patient's 105 change in speech. If the medical records indicate the patient 105 is a smoker with a clean family history, then cancer can be considered a more likely cause than other hereditary causes.

Auxiliary data sources 115 need not be only health-related. As the world becomes more and more electronically connected, the speech-based health monitor 130 can be configured to request and/or receive real-time auxiliary data 120 from auxiliary data sources 115 such as purchase data from a store's point-of-sale (POS) system, product information for a purchased product, or the hospital closest to the current location of the patient 105. Such examples will be discussed in more detail later in the Figures.

In another contemplated embodiment, the speech-based health monitor 130 can be used in conjunction with a targeted advertising application or system. In such an embodiment the speech-based health monitor 130 can passively capture a speech segment 170 when the patient 105 is submitting audio data to the client device 110 for another purpose, such as during a phone conversation, creating a voice memo, or issuing voice commands to the client device 110. The speech-based health monitor 130 can then provide its analysis of the speech segment 170 to the targeted advertising system in order to customize the types of advertisements that are presented to the patient 105. In such an embodiment, the diagnostic data 165 can define common ailments or conditions in terms of speech quality parameters.

For example, analysis of a speech segment 170 can indicate that the patient 105 is experiencing nasal congestion. Since it is spring and the patient 105 is relatively healthy, the speech-based health monitor 130 can determine that the patient 105 is most likely suffering from allergies or a cold. Thus, the targeted advertising system can be notified and present the patient 105 with advertisements for various cold and allergy medicines.

In another embodiment, the speech-based health monitor 130 can be used as a means of respiratory health verification. Such an embodiment can be beneficial for industrial settings whose processes utilize or generate caustic fumes; exposure from an incident can be recognized and treated faster than conventional approaches. Additionally, such an embodiment could be easily integrated into a health insurance quotation process; detected problems can verify the candidate's questionnaire answers as well as influence calculations.

For example, an insurance candidate can indicate that they are a non-smoker on an electronic questionnaire. Based upon the questionnaire, the health insurance application can calculate an expected insurance rate for the candidate. Analysis of the candidate's submitted speech segment 170 can detect a jitter (vocal fold vibration variability) of a magnitude often seen in smokers. Based on this analysis, the health insurance application can adjust the expected insurance rate to that of a smoker and, possibly, require medical verification of non-smoker status.

In yet another embodiment, the functionality of the speech-based health monitor 130 can be expanded to include additional systems for the analysis of other media input, such as video or digital images. For example, speech segment 170 analysis can indicate an irregular pronunciation of words. The speech-based health monitor 130 can request that the patient 105 submit a digital image of their face. The submitted image would then be analyzed by an image analysis system to determine if the patient 105 is experiencing swelling in their face, particularly their lips, which could indicate anaphylaxis.

In one embodiment, the initial information (video, images, speech) can be captured from a client-device, such as a mobile phone or desktop computer. The "escalation" of going from a "passive" health capture mode to a more active one (asking a patient to take a video of themselves, for example) can occur responsive to an initial analysis (based exclusively on speech) indicating a potential health risk exists (exceeds a predetermined likelihood threshold). The prompting of additional information can occur via a health-specific application (running on the mobile phone, tablet, or other device 110). The additional information can even include responses to questions, which the patient 105 (user of the phone) is prompted to answer.

In a further situation, when one or more of the information data points indicates a substantial likelihood of a health risk, a patient can be prompted (via the mobile phone, or other device) to travel to a nearby kiosk (e.g., a health assessment station within a grocery store or a clinic for example) in order that a more accurate assessment (based on more fine-grained information) can be conducted. When the device through which the patient 105 interacts includes a GPS or other location based mechanism, directions and other guidance to the nearby kiosk or other health assessment station (which can even include a nearby emergency room) can be provided.

In one embodiment, instead of guiding a patient 105 to a kiosk or other health assessment station, the patient 105 can be interactively connected to a health assessment expert (or system). For example, the patient 105 can be dynamically connected with a medical expert via a video teleconference so that the patient 105 receives professional medical advice (beyond what is provided through the automatic health assessment). The remote party (medical professional and/or system) can be automatically provided with the health assessment results, which triggered the communication. These health assessment results may be provided in a different form for the medical expert (with greater or lesser detail, typically greater and more technical as this level of granularity is likely unhelpful to a typical patient 105; situations where lesser information is transmitted may be to protect the privacy of the patient 105). The medical expert can leverage this provided information to more accurately (and quickly) assess a health of the patient 105.

The above functionality may be integrated into a health insurer's application (running on end-users devices) in one embodiment. In another embodiment, the device providing a patient assessment 105 may be a medical assessment device assisting a nurse, nurse practitioner, an EMT technician working in a clinic (in cooperation with a remotely located doctor). Such a device/capability can be significantly of aid to schools, nursing homes, and other venues where a health of a resident is sometimes determined by a human agent having a rudimentary medical knowledge. Similarly, an application can be used by novices trained in RedCross® techniques for emergency care, where properly following the application/advice given through the application can minimize potential liability for the "Good Samaritan" assistant and can provide this person with additional and needed tools.

It is important to emphasize the superiority of embodiments of the present invention over conventional systems that utilize speech analysis for diagnostic purposes. Many conventional systems utilize speech recognition to match a speech segment 170 submitted by a patient 105 to an exemplar speech segment contained in a collective library of speech segments that represent various speech pathologies.

While this approach has diagnostic benefit and can be used as an additional component in expanded embodiments of the present invention (as previously discussed), it can only provide a generic analysis of a single data point. The present invention can provide patient-specific analyses based upon the comparison with the speech segment baseline 152 and/or speech segment history 154 that are generated by the patient 105. This approach can increase the accuracy of diagnosis determined using the speech-based health monitor.

Further, the speech-based health monitor can include tools for providing analyses of the period of time encompassed by the speech segment history 154. Again, these analyses can be patient-specific and can lend themselves to correlation with other personnel and/or health issues experienced by the patient 105.

Network 180 can include any hardware/software/and firmware necessary to convey data encoded within carrier waves. Data can be contained within analog or digital signals and conveyed though data or voice channels. Network 180 can include local components and data pathways necessary for communications to be exchanged among computing device components and between integrated device components and peripheral devices. Network 180 can also include network equipment, such as routers, data lines, hubs, and intermediary servers which together form a data network, such as the Internet. Network 180 can also include circuit-based communication components and mobile communication components, such as telephony switches, modems, cellular communication towers, and the like. Network 180 can include line based and/or wireless communication pathways.

As used herein, presented data store 145 and auxiliary data sources 115 can be a physical or virtual storage space configured to store digital information. Data store 145 and auxiliary data sources 115 can be physically implemented within any type of hardware including, but not limited to, a magnetic disk, an optical disk, a semiconductor memory, a digitally encoded plastic memory, a holographic memory, or any other recording medium. Data store 145 and auxiliary data sources 115 can be a stand-alone storage unit as well as a storage unit formed from a plurality of physical devices. Additionally, information can be stored within data store 145 and auxiliary data sources 115 in a variety of manners. For example, information can be stored within a database structure or can be stored within one or more files of a file storage system, where each file may or may not be indexed for information searching purposes. Further, data store 145 and/or auxiliary data sources 115 can utilize one or more encryption mechanisms to protect stored information from unauthorized access.

Figure 2:
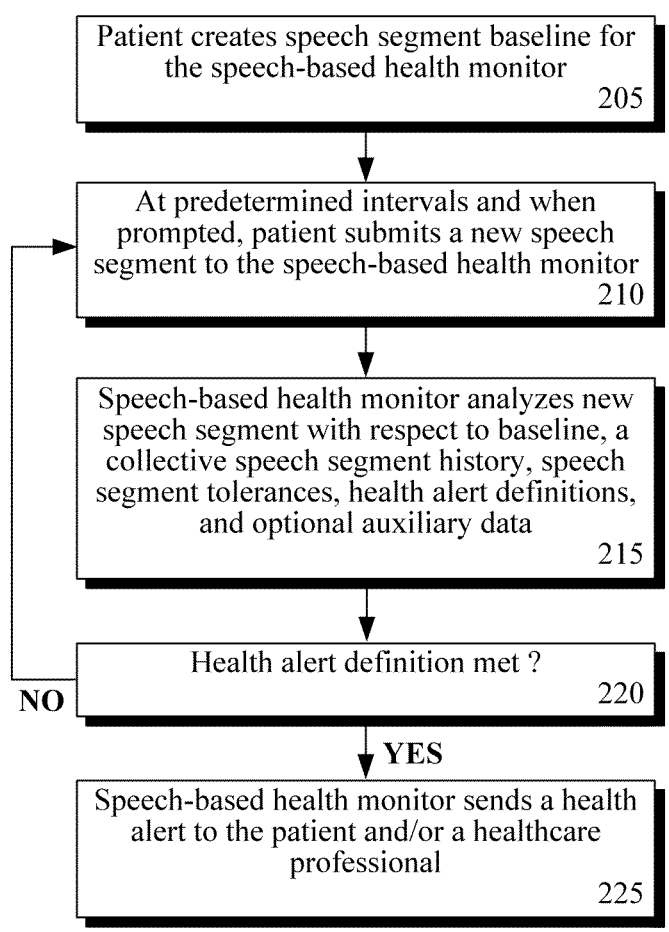
FIG. 2 is a flowchart of a method describing the high-level interactions for using the speech-based health monitor in accordance with an embodiment of the inventive arrangements disclosed herein.

FIG. 2 is a flowchart of a method 200 describing the high-level interactions for using the speech-based health monitor in accordance with embodiments of the inventive arrangements disclosed herein. Method 200 can be performed within the context of system 100.

Method 200 can begin in step 205 where the patient can create a speech segment baseline for the speech-based health monitor. At predetermined intervals and when prompted, the patient can submit a new speech segment to the speech-based health monitor in step 210. In step 215, the speech-based health monitor can analyze the new speech segment with respect to the speech segment baseline, the patient's collective speech segment history, speech segment tolerances, health alert definitions, and optional auxiliary data.

In step 220, it can be determined if the analysis of the speech segment has met one or more health alert definitions. When a health alert definition has not been met, flow of method 200 can return to step 210 where the speech-based health monitor awaits the next speech segment submission. When a health alert definition has been met, the speech-based health monitor can send a health alert to the patient and/or a designated healthcare professional in step 225.

It should be noted that, although the interactions and functionality described in method 200 and subsequent methods are described in terms of doctor-patient, the functionality of the speech-based health monitor can be expanded to incorporate interaction with non-medical systems that require a cursory medical opinion of a person based upon their speech.

For example, a sales kiosk in a pharmacy can utilize the analysis provided by the speech-based health monitor to judge the type and/or severity of a customer's current ailment. That is, the sales kiosk can recommend a cold medicine with a nasal decongestant if nasal congestion is detected or one with a pain reliever if the hoarseness of a sore throat is detected.

In one embodiment, this type of screening can permit a new "level" of control for pharmaceuticals. For example, for controlled (but not prescription pharmaceuticals), such as Sudafed® some additional level of screening based on a health analysis of a purchaser can be performed. Such a screening can greatly minimize risks of disseminating certain pharmaceuticals or substances for illicit purposes (e.g., using controlled substances to produce a Methamphetamine, for example).

Figure 3:
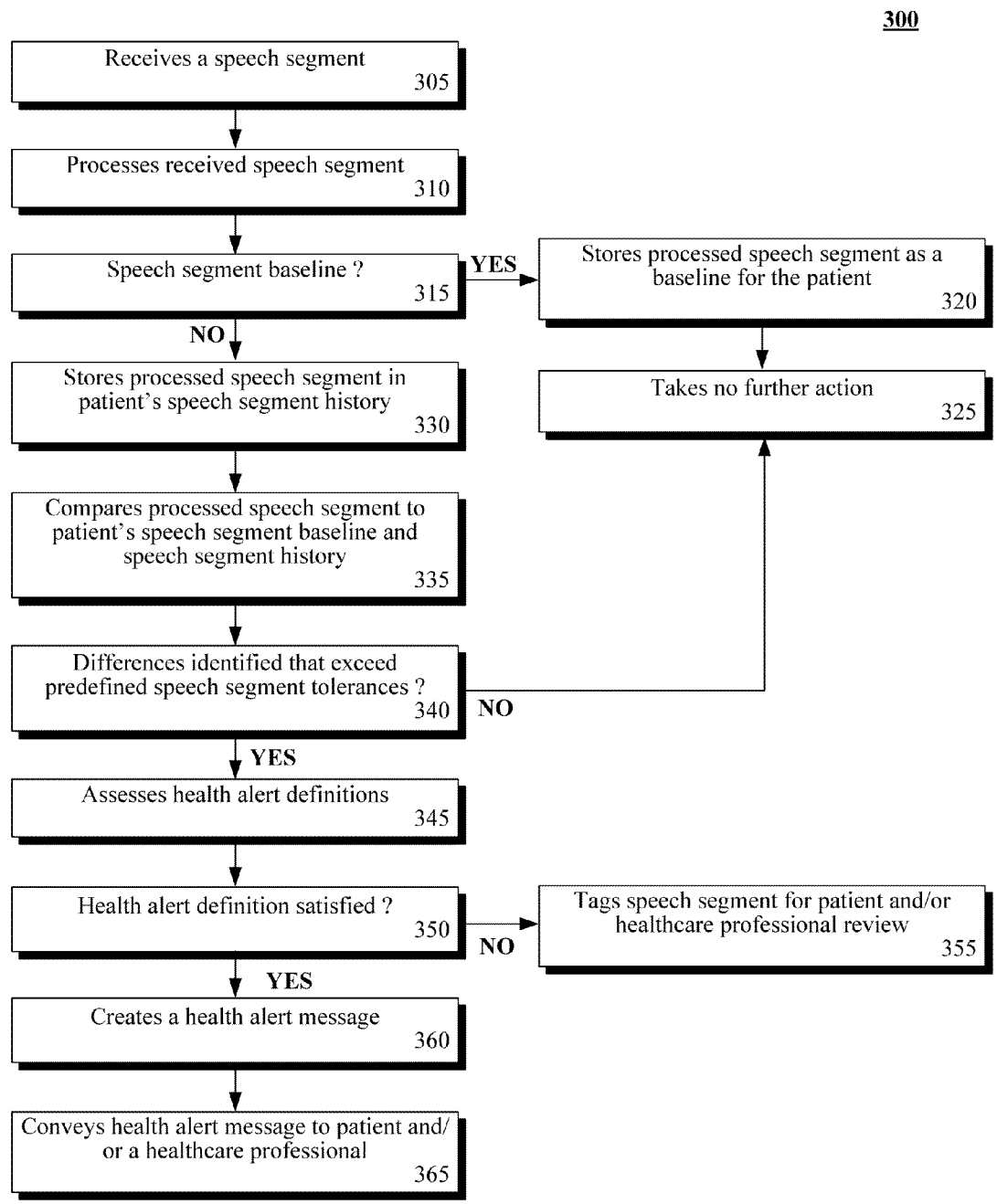
FIG. 3 is a flowchart of a method detailing operation of the speech-based health monitor in accordance with an embodiment of the inventive arrangements disclosed herein.

FIG. 3 is a flowchart of a method 300 detailing operation of the speech-based health monitor in accordance with embodiments of the inventive arrangements disclosed herein. Method 300 can be performed within the context of system 100 and/or method 200.

Method 300 can begin in step 305 where the speech-based health monitor can receive a speech segment. The received speech segment can be processed in step 310. In step 315, it can be determined if the received speech segment is to be used as a speech segment baseline.

When the speech segment is to be used as a baseline, step 320 can execute where the processed speech segment is stored as a baseline for the patient. No further action need to be taken by the speech-based health monitor in step 325. In an alternate embodiment, the speech segment baseline can be analyzed for existing pathologies prior to the execution of step 325.

When the speech segment is not to be used as a baseline, step 330 can be performed where the processed speech segment can be stored in the patient's speech segment history. The processed speech segment can be compared to the patient's speech segment baseline and speech segment history in step 335.

In step 340, it can be determined if differences have been identified within the processed speech segment that exceed the predefined speech segment tolerances. When the determined differences do not exceed the speech segment tolerances, flow of method 300 can proceed to step 325 where no further action is taken by the speech-based health monitor.

When the determined differences exceed one or more speech segment tolerances, the health alert definitions can be assessed in step 345. In step 350, it can be determined if a health alert definition has been satisfied. When none of the health alert definitions have been satisfied, the speech segment can be tagged for review by the patient and/or a healthcare professional in step 355.

When a health alert definition has been satisfied, step 360 can execute where a health alert message can be created. The health alert message can be conveyed to the patient and/or healthcare professional in step 365.

Figure 4:
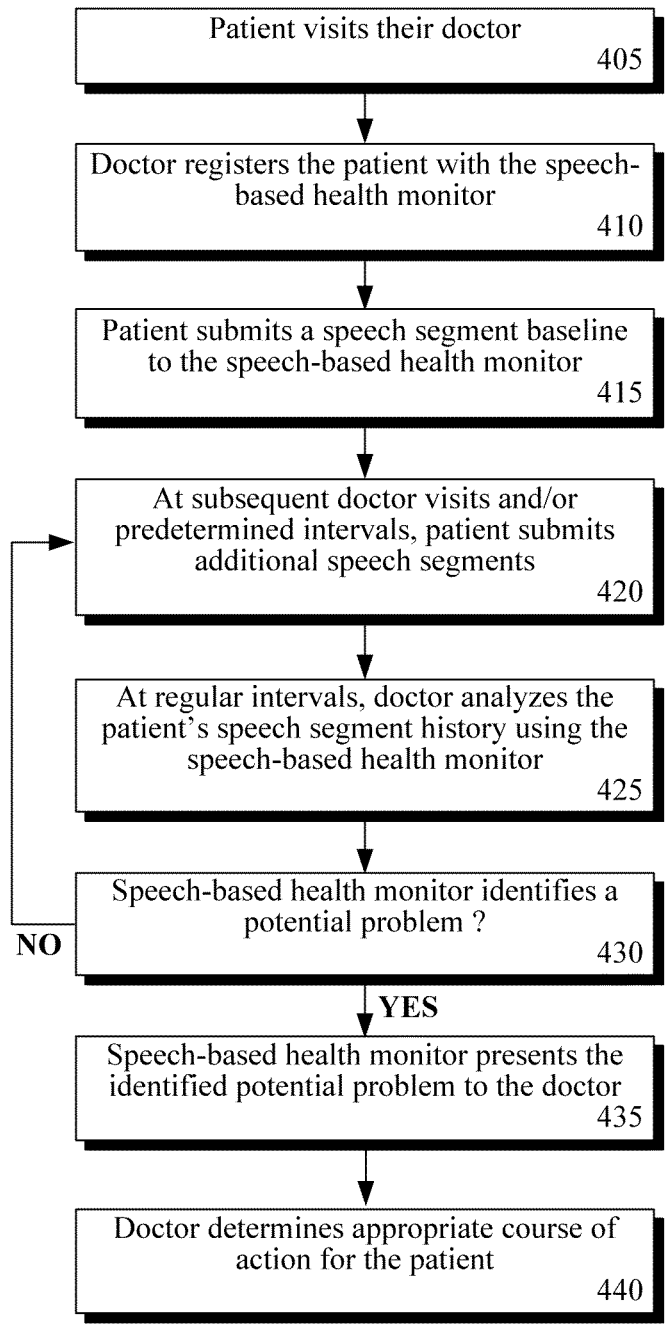
FIG. 4 is a flowchart of a method describing a general example for using the speech-based health monitor in accordance with embodiments of the inventive arrangements disclosed herein.

FIG. 4 is a flowchart of a method 400 describing a general example for using the speech-based health monitor in accordance with embodiments of the inventive arrangements disclosed herein. Method 400 can be performed within the context of system 100 and/or method 200 and/or in conjunction with method 300.

Method 400 can begin in step 405 where a patient can visit their doctor. The doctor can register the patient with the speech-based health monitor in step 410. A registration process for the speech-based health monitor can include the entry of data items specific to the patient as well as defining parameters for handling health alerts.

In step 415, the patient can submit a speech segment baseline to the speech-based health monitor. Step 415 can be included within the registration process of step 410; however, in this example, it can be listed separately to emphasize the need for establishing a speech segment baseline prior to regular use by the patient.

At subsequent doctor visits and/or predetermined intervals, the patient can submit additional speech segments to the speech-based health monitor in step 420. Step 420 can illustrate that collection techniques used to capture speech segments can differ based upon the specific doctor and/or healthcare facility.

For example, a patient may not have access to a smart phone. The equipment necessary for their participation with the speech-based health monitor can reside in their doctor's office or clinic where the patient can visit to submit speech segments. Alternately, a patient with access to a smart phone can remotely submit subsequent speech segments using the smart phone.

At regular intervals, the doctor can analyze the patient's speech segment history using the speech-based health monitor in step 425. In step 430, it can be determined if the speech-based health monitor has identified a potential problem. When the speech-based health monitor has not identified a potential problem, flow of method 400 can return to step 420 where the patient continues to submit speech segments.

When the speech-based health monitor has identified a potential problem, the speech-based health monitor can present the identified potential problem to the doctor in step 435. In step 440, the doctor can then determine the appropriate course of action for the patient.

Figure 5:
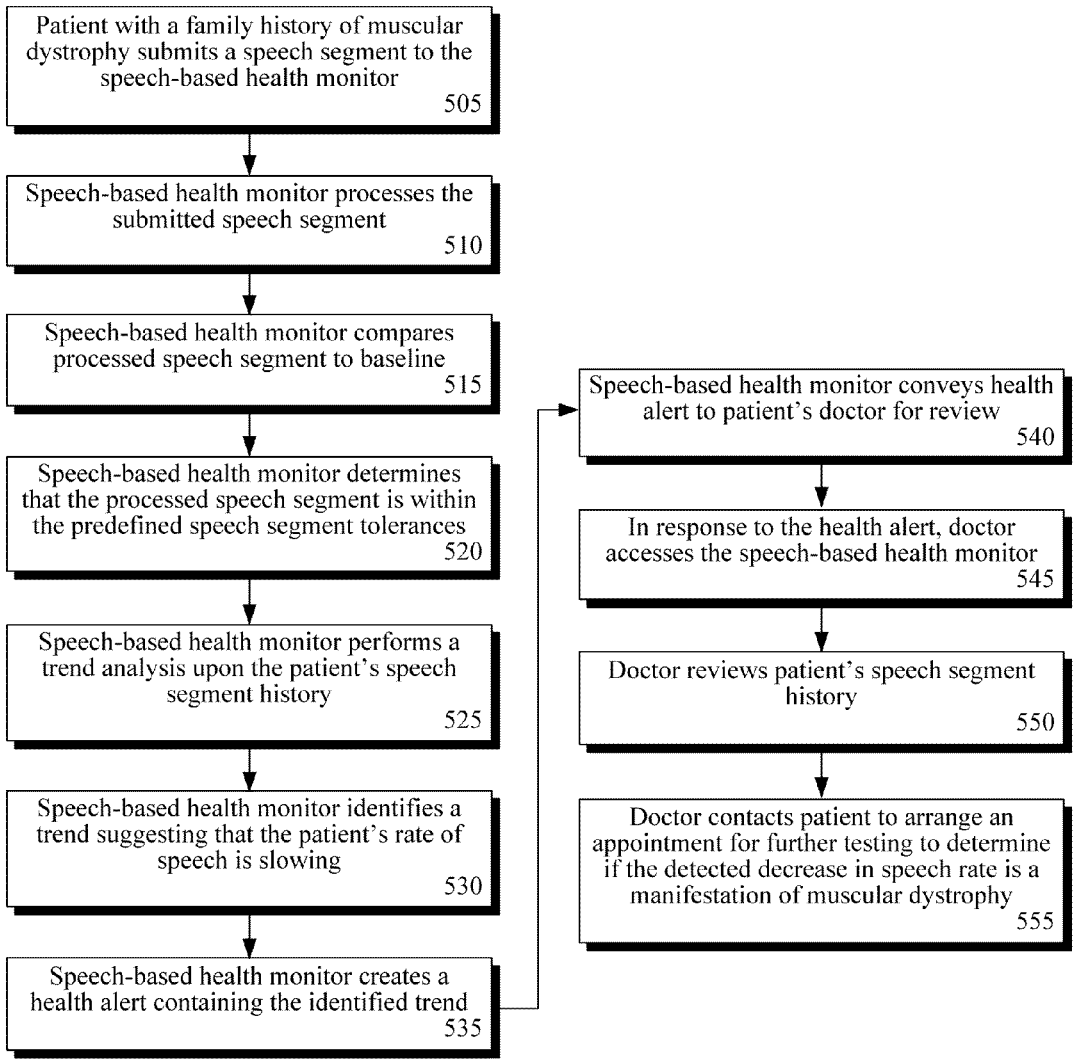
FIG. 5 is a flowchart of a method expressing a detailed example of the usage of the speech-based health monitor in accordance with embodiments of the inventive arrangements disclosed herein.

FIG. 5 is a flowchart of a method 500 expressing a detailed example of the usage of the speech-based health monitor in accordance with embodiments of the inventive arrangements disclosed herein. Method 500 can be a specific example of methods 200, 300, and/or 400.

Method 500 can begin in step 505 where a patient with a family history of muscular dystrophy can submit a speech segment to the speech-based health monitor. In method 500, it can be assumed that the patient has already established a speech segment baseline and speech segment history.

The speech-based health monitor can process the submitted speech segment in step 510. In step 515, the speech-based health monitor can compare the processed speech segment to the corresponding speech segment baseline. The speech-based health monitor can determine that the processed speech segment is within the predefined speech segment tolerances in step 520.

In step 525, the speech-based health monitor can perform a trend analysis of the patient's speech segment history. A trend suggesting that the patient's rate of speech is slowing can be identified by the speech-based health monitor in step 530. In step 535, the speech-based health monitor can create a health alert containing the identified trend.

The health alert can be conveyed from the speech-based health monitor to the patient's doctor for review in step 540. In response to the health alert, the doctor can access the speech-based health monitor in step 545. In step 550, the doctor can review the patient's speech segment history. The doctor can then contact the patient to arrange an appointment for further testing, in step 555, to determine if the detected decrease in speech rate is a manifestation of muscular dystrophy.

Figure 6:
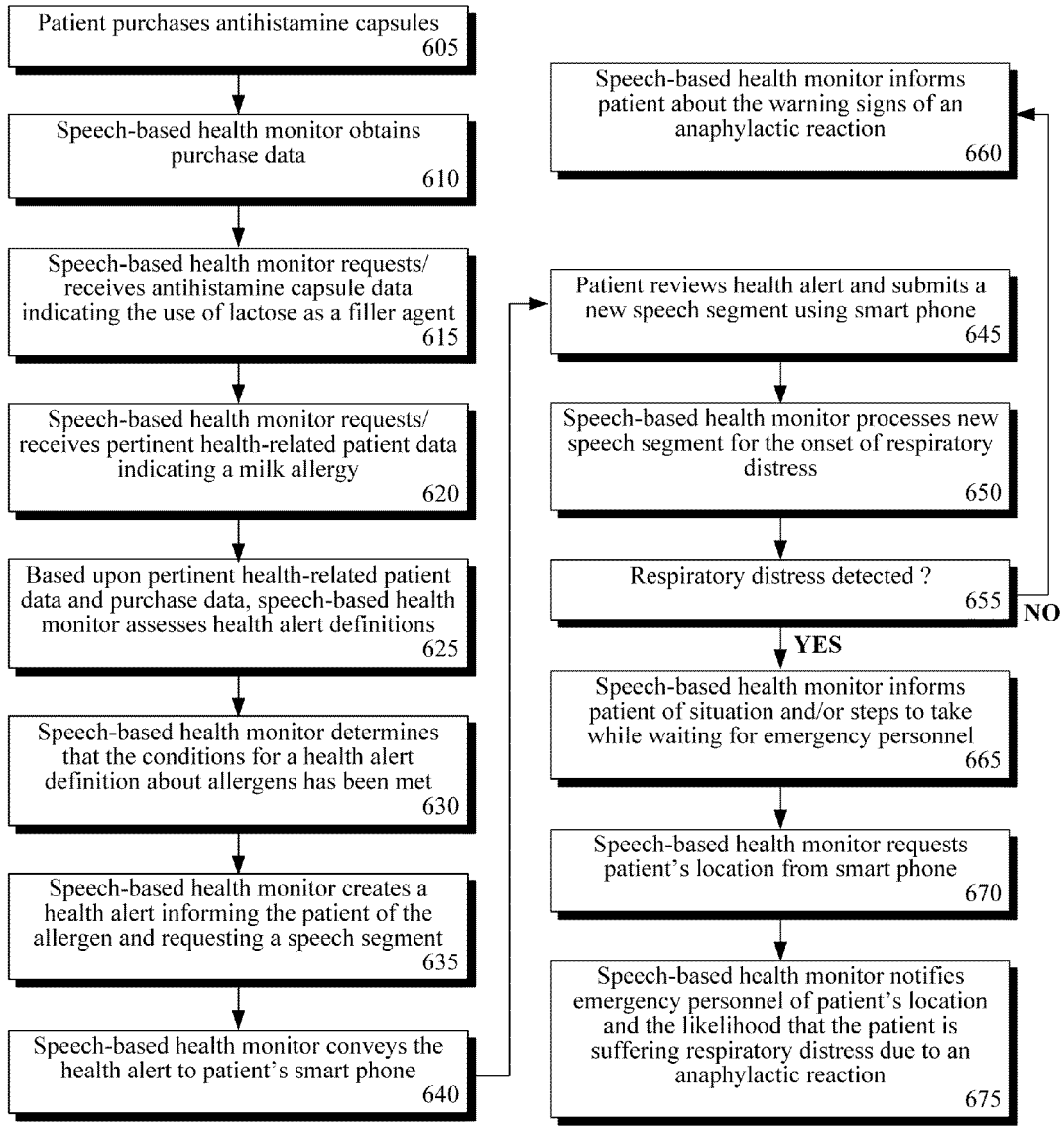
FIG. 6 is a flowchart of a method presenting a detailed example of the use of external auxiliary data with the speech-based health monitor in accordance with embodiments of the inventive arrangements disclosed herein.

FIG. 6 is a flowchart of a method 600 presenting a detailed example of the use of external auxiliary data with the speech-based health monitor in accordance with embodiments of the inventive arrangements disclosed herein. Method 600 can be performed within the context of system 100 and/or in conjunction with methods 200, 300, 400, and/or 500.

Method 600 can begin in step 605 where a patient can purchase antihistamine capsules. The speech-based health monitor can obtain the corresponding purchase data in step 610. The manner in which the speech-based health monitor obtains the patient's purchase data can depend upon the specific configuration and/or implementation of the speech-based health monitor. In this example, the speech-based health monitor can obtain the purchase data in real-time or near real-time; else, the assistance facilitated by the speech-based health monitor can be no longer pertinent to the patient.

For example, during the registration process, the patient can be able to provide the speech-based health monitor with permissions or authorization to access purchase data from their bank. Alternately, such information can be made readily available to the speech-based health monitor via the patient's smart phone, particularly when using a virtual wallet or other such application that handles purchases local to the smart phone.

In step 615, the speech-based health monitor can request and receive data about the antihistamine capsules that indicates that lactose is used as a filler agent. The data about the antihistamine capsules mentioned in step 615 can be obtained from a variety of sources such as the manufacturer's Web site or a government Web site like those maintained by the Federal Drug Administration or National Institutes of Health.

The speech-based health monitor can request and receive pertinent health-related patient data in step 620, which, in this example, indicates that the patient has a milk allergy. The pertinent patient data can be obtained from a patient profile associated with the speech-based health monitor that contains such information or from a remote data source like a doctor's database housing the patient's medical records; access to this type of information can be dependent upon the patient, healthcare professional's data system, and/or the specific configuration or implementation of the speech-based health monitor.

In step 625, the speech-based health monitor can assess the health alert definitions using the pertinent health-related patient data and purchase data. Step 625 can include analysis that deduces outcomes of the intersection or combination of elements contained in the pertinent health-related patient data and purchase data.

In this specific example, the speech-based health monitor can determine, in step 630, that the conditions for a health alert definition about allergens has been met. That is, in this example, a health alert definition having a single triggering condition of the patient is having an allergic reaction or the patient is in a situation likely to cause the patient to have an allergic reaction can be evaluated as TRUE. Step 630 can result in the speech-based health monitor executing the subsequent steps of method 600 that represent the actions defined for the satisfied health alert definition.

In step 635, the speech-based health monitor can create a health alert that informs the patient of the allergen in the antihistamine capsules and requests that the patient immediately submit a speech segment for analysis. The speech-based health monitor can convey the health alert to the patient's smart phone or another designated device in step 640.

In step 645, the patient can review the health alert and submit a new speech segment to the speech-based health monitor using their smart phone. The speech-based health monitor can process the new speech segment submitted by the patient for changes that can indicate the onset of respiratory distress that are associated with an allergic reaction or anaphylaxis in step 650.

In step 655, the speech-based health monitor can determine if the speech segment indicates respiratory distress. When the analysis of the speech segment does not indicate respiratory distress, the speech-based health monitor can inform the patient about the warning signs of an anaphylactic reaction in step 660. Step 660 can further include the speech-based health monitor scheduling submission of a follow-up speech segment after a predetermined time interval to recheck the condition of the patient's respiratory system.

When analysis of the speech segment indicates the onset of respiratory distress, step 665 can be performed where the speech-based health monitor informs the patient that of their situation (i.e., "You are experiencing an allergic reaction.") and/or steps that the patient can take while waiting for emergency personnel (i.e., "Please sit in an upright position and try to remain calm."). The speech-based health monitor can request the current location of the patient from the patient's smart phone in step 670.

In step 675, the speech-based health monitor can notify emergency personnel of the patient's location and the likelihood that the patient is suffering respiratory distress due to an anaphylactic reaction. It is also possible, in step 675, for the speech-based health monitor to provide the emergency personnel with additional medical information about the patient like allergy information or other data that could affect the patient's care.

Similarly, the speech-based health monitor can perform searches qualified by the patient's current location and/or situation to provide additional guidance. For example, based upon the patient's current location, the speech-based health monitor can advise the patient to drive three blocks to a hospital; a faster course of action than waiting for emergency personnel to arrive.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method comprising:
    indexing, by a computer comprising hardware and software executing on the hardware, a plurality of health conditions of a human against a plurality of different health-related speech characteristics;
    identifying, by the computer, a speech segment of a speaker;
    analyzing, by the computer, the speech segment to determine a presence or absence of any of the health-related speech characteristics;
    upon determining a presence of one of the health-related speech characteristics, determining, by the computer, a corresponding one of the health conditions consistent with the indexing; and
    generating, by the computer, an alert indicating that the speaker has a statistically significant likelihood of having the determined health condition based on results of the analyzing, wherein the speech segment is received from mobile computing device of the speaker, wherein the alert triggers an advertisement specific to the determined health condition to be sent over a network for presentation on the mobile communication device.

2. The method of claim 1, further comprising:
    registering the speaker with a speech-based health monitor; and
    establishing a speech segment baseline representing an initial state of the speaker, said state being a state where the speaker is in relatively good health, wherein the health-related speech characteristics represent speaker specific deviations from the speech segment baseline.

3. The method of claim 1, further comprising:
    storing a plurality of audio segments for the speaker while the speaker is in an initial state of health, said audio segments being part of a speech history specific to the speaker, wherein the determining of the presence of the health-related speech characteristics is based on deviations between the health-related speech characteristics in the speech segment and the audio segments of the speech history.

4. The method of claim 1, wherein the alert is one of a set of different health alerts, said health alert being triggered responsive to conditions of a corresponding health alert definition being satisfied, said method further comprising:

executing at least one action associated with the at least one satisfied health alert definition.

5. The method of claim 1, wherein the analyzing compares respiratory specific characteristics of the speech segment against an excepted baseline for respiratory specific characteristics anticipated for a healthy respiratory state of the human, wherein the determined health condition is one that has altered a respiratory state of the human as determined by analyzing the speech segment to an unhealthy respiratory state as contrasted with the healthy respiratory state.

6. The method of claim 1, wherein the speaker is an individual insured by or seeking to be insured by a health insurance provider, wherein the generated alert triggers an event in a computing system of the health insurance provider that:

raises a cost of health insurance for the speaker in a manner consistent with the likelihood that the speaker has the determined health condition;

denies health insurance for the speaker based on the likelihood that the speaker has the determined health condition; or requires the speaker to undergo testing by a medical professional to assess whether or not the speaker has the determined health condition, wherein in absence of the determined health condition from the analyzing no testing by medical professionals would be required by the health insurance provider.

7. The method of claim 1, further comprising:

responsive to the alert, providing a computing device of the speaker with a request for additional data relating to the health of the speaker;

receiving the additional data; and analyzing the additional data to make a more accurate assessment regarding whether the speaker has the determined health condition or not.

8. The method of claim 7, wherein the additional data comes from an image or video capture mechanism of a device used by the speaker, said device being a device from which audio for the speech segment was acquired.

9. The method of claim 1, further comprising:

processing the speech segment of the speaker to obscure spoken words contained in the speech segment while retaining content for detecting the health-related speech characteristics.

10. The method of claim 1, wherein the detected health-related speech characteristic indicates that the speaker is a smoker, is pregnant, or has a sinus blockage.

11. The method of claim 1, wherein the analyzing determines from the speech segment that there has been a weakening in the lavatory palatine of the speaker.

12. The method of claim 1, wherein the analyzing determines there is a problem relating to the primary muscle for moving a velum of the speaker.

13. The method of claim 1, wherein the health condition is one indicated by a respiratory or laryngeal problem ascertained by the analyzing.

14. The method of claim 1, wherein the health condition indicates a presence of mucus in the body of the speaker, or wherein the health condition is that the speaker has the statistically significant likelihood of having a tumor in their respiratory system.

15. A method for using speech analysis to detect speech pathologies comprising:

registering a patient with a speech-based health monitor;

establishing a speech segment baseline representing an initial state of the patient's speech with the speech-based health monitor;

when prompted by the speech-based health monitor, submitting of a speech segment to the speech-based health monitor by the patient, wherein the submitted speech segment represents a current state of the patient's speech system;

analyzing of the submitted speech segment by the speech-based health monitor with respect to at least one of the established speech segment baseline and a speech segment history associated with the patient, wherein the speech segment history comprises speech segments previously submitted by the patient;

based upon said analysis, determining of a satisfaction of at least one health alert definition by the speech-based health monitor, wherein a health alert definition defines at least one action performed by the speech-based health monitor when its associated triggering conditions are satisfied by the analysis; and executing the at least one action associated with the at least one satisfied health alert definition.

16. The method of claim 15, wherein establishing of the speech segment baseline further comprises:

storing the speech segment baseline within a data store of the speech-based health monitor, wherein the stored speech segment baseline is associated with the patient.

17. The method of claim 15, wherein submitting of the speech segment to the speech-based health monitor further comprises:

adding the submitted speech segment to the speech segment history of the patient within a data store of the speech-based health monitor.

18. The method of claim 15, wherein analyzing the submitted speech segment further comprises:

comparing the submitted speech segment with the established speech segment baseline;

when results of said comparison indicate at least one difference between the submitted speech segment and the established speech segment baseline, determining whether each indicated difference is within a corresponding predefined speech segment tolerance, wherein said predefined speech segment tolerance expresses a maximum value that a speech characteristic of the submitted speech segment is allowed to deviate from the established speech segment baseline;

when each indicated difference of the speech segment is within its corresponding predefined speech segment tolerance, canceling the determination of the satisfaction of at least one health alert definition and the execution of the at least one action associated with the at least one satisfied health alert definition, wherein the speech-based health monitor awaits a new submission of the speech segment from the patient; and when at least one indicated difference of the speech segment is outside its corresponding predefined speech segment tolerance, proceeding with the determination of the satisfaction of at least one health alert definition.

19. The method of claim 1, wherein determining of the satisfaction of at least one health alert definition further comprises:

identifying the satisfaction of only a default health alert definition, wherein a situation is created where a health alert definition to handle said analysis is undefined;

indicating that the speech segment is unable to be handled by current health alert definitions, wherein said speech segment is marked within the speech segment history with an identifier that instructs the speech-based health monitor to ignore the speech segment for analysis purposes; and requesting resolution of the marked speech segment from a designated entity; and upon receipt of resolution for the marked speech segment, removing the identifier from the speech segment in the speech segment history.

20. A computer program product comprising a non-transitory computer readable storage medium having computer usable program code embodied therewith and executed by one or more processors of the computer, the computer usable program code comprising:

computer usable program code configured to establish a speech segment baseline representing an initial state of a patient's speech system;

computer usable program code configured to receive a speech segment from the patient, wherein the speech segment represents a current state of the patient's speech system;

computer usable program code configured to analyze the received speech segment with respect to at least one of the established speech segment baseline and a speech segment history associated with the patient, wherein the speech segment history comprises speech segments previously submitted by the patient;

computer usable program code configured to, based upon said analysis, determine satisfaction of at least one health alert definition, wherein a health alert definition defines at least one action to be performed when its associated triggering conditions are satisfied by the analysis; and computer usable program code configured to execute the at least one action associated with the at least one satisfied health alert definition.

\* \* \* \* \*